Jan. 15, 1957 J. L. CRANDALL Plant Pat. 1,551
APRICOT TREE
Filed Sept. 21, 1955
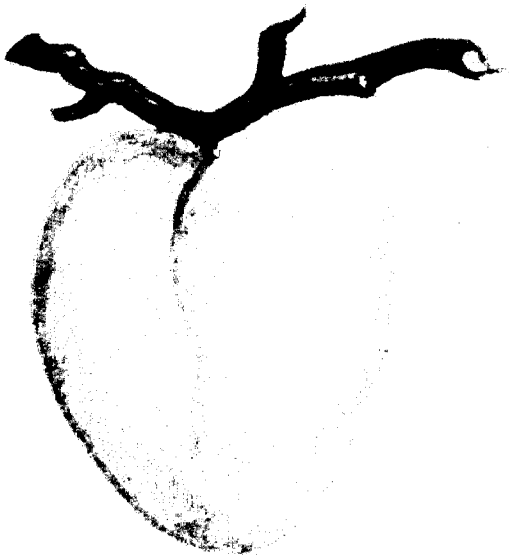
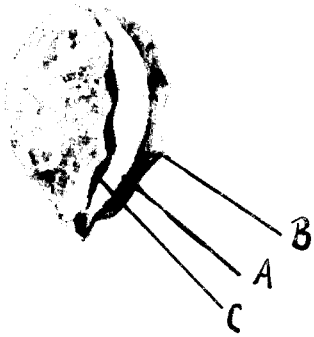
INVENTOR
Judson L. Crandall
By Orville M. Kile
PLANT PATENT AGENT United States Patent Office Plant Pat. 1,551
Patented Jan. 15, 1957

1,551

APRICOT TREE

Judson L. Crandall, Hanford, Calif.

Application September 21, 1955, Serial No. 535,778

1 Claim. (Cl. 47—62)

My present invention relates to a new and useful variety of apricot tree and particularly to the improvement of the fruit borne by the tree. Its novelty consists principally in the early maturity and sweet flavor of its fruit, the pit also having distinctive characteristics.

My new variety originated as a second-generation seedling. I planted a seed from a Tilton tree (not patented) grown on my property in Hanford. Although the pollen parent of the resulting seedling is unknown, it probably was also the Tilton variety. In due time this seedling fruited and I planted several of its seeds, one of which produced a seedling resulting in the present variety. The pollen parent of the final seedling also probably was Tilton.

I have asexually reproduced my new variety at my home property by means of budding, and the distinguishing characteristics appear to be firmly fixed.

The accompanying illustration is a full-color painting of one of the fruits and one of the seeds of my new variety, drawn approproximately to the same scale. In the painting of the seed, the ridge marked "A" represents the natural cleavage line, with "B" and "C" representing the two prominent ridges parallel thereto.

There appear to be no differences between my new variety and the variety Tilton, with reference to growth habits, tree appearance, leaves, or blossoms—the only known differences being in the date of blossoming, the maturity and flavor of the fruit and the prominently ridged pits or seeds.

This new variety blossoms about two weeks earlier than the Tilton variety, occurring around March 1st in the present year in the location mentioned. Careful examination of the leaves of this new variety and its ancestor, Tilton, discloses no differences, either in glands, finely serrated edges, texture, or veining.

In the following description of the fruit, color plate numbers refer to Ridgway's Color Standards and Nomenclature. Other color references are to the ordinary dictionary meaning of the term.

FRUIT

*Maturity.*—About two weeks earlier than Tilton.

*Size.*—Axial diameter averages 1½ to 1¾ inches.

*Shape.*—Somewhat elongated. Base and apex rounded. Cavity narrow and rather deep.

*Skin.*—Tender. Almost completely smooth. Usual apricot color, approximately Capucine Yellow (Plate XII).

*Flesh.*—Juicy. Tender, with few fibers. Color of flesh approximately same as that of skin.

*Flavor.*—Very sweet and mild-flavored, with no acid taste. (Much sweeter than Tilton.)

*Stone.*—Free. Relatively small. Has prominent ridges on both sides of the median ridge that marks the cleavage lines of the pit.

Having thus disclosed my invention, I claim:

The new and distinct variety of apricot tree, substantially as herein described and illustrated, substantially like the Tilton variety as to size, shape and foilage of tree, but characterized especially by its early blossoming and by the novelty of its fruit, particularly its early maturity, exceptionally sweet flavor, and having pits showing three prominent ridges as illustrated.

No references cited.